US010163270B2

(12) United States Patent
Gotte et al.

(10) Patent No.: US 10,163,270 B2
(45) Date of Patent: *Dec. 25, 2018

(54) METHOD FOR DETERMINING CONTACT POSITION PARAMETERS OF A JOINT CONNECTING TWO BONES

(71) Applicant: Brainlab AG, Munich (DE)

(72) Inventors: Hubert Gotte, Munich (DE); Lars Dohmen, Munich (DE)

(73) Assignee: Brainlab AG, Munich (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/395,247

(22) Filed: Dec. 30, 2016

(65) Prior Publication Data

US 2017/0178413 A1 Jun. 22, 2017

Related U.S. Application Data

(63) Continuation of application No. 14/362,988, filed as application No. PCT/EP2012/061757 on Jun. 20, 2012, now Pat. No. 9,865,095.

(30) Foreign Application Priority Data

Dec. 9, 2011 (WO) ................ PCT/EP2011/072323
Dec. 9, 2011 (WO) ................ PCT/EP2011/072324

(51) Int. Cl.
*A61B 5/00* (2006.01)
*A61B 5/103* (2006.01)
(Continued)

(52) U.S. Cl.
CPC ............... *G06T 19/20* (2013.01); *A61B 5/11* (2013.01); *A61B 5/4528* (2013.01);
(Continued)

(58) Field of Classification Search
CPC ....... A61B 5/4528; A61B 5/103; A61B 17/154; G06F 17/50
See application file for complete search history.

(56) References Cited

U.S. PATENT DOCUMENTS

| 2002/0087274 | A1 | 7/2002 | Alexander |
| 2005/0251065 | A1 | 11/2005 | Henning et al. |
| 2008/0269596 | A1 | 10/2008 | Revie et al. |
| 2009/0157083 | A1 | 6/2009 | Park et al. |
| 2009/0209884 | A1* | 8/2009 | Van Vorhis ............. G06F 19/34 600/595 |

(Continued)

FOREIGN PATENT DOCUMENTS

| WO | 2009076296 A2 | 6/2009 |
| WO | 2013/083201 | 6/2013 |

OTHER PUBLICATIONS

International Search Report and Written Opinion for International Application No. PCT/EP2012/061757 dated Sep. 19, 2012.

(Continued)

Primary Examiner — Matthew Salvucci
(74) Attorney, Agent, or Firm — Middleton Reutlinger

(57) ABSTRACT

A data processing method for determining six parameters, corresponding to six degrees of freedom, of a contact position of a joint which connects two bones, comprising the steps of acquiring a 3D model of each bone, acquiring four of the six parameters as a given parameters, selecting initial values for the two remaining parameters and varying the two remaining parameters virtually in order to achieve a virtual relative position between the two 3D models such that they are in contact with each other.

17 Claims, 10 Drawing Sheets

(51) Int. Cl.
   *A61B 17/15*    (2006.01)
   *G06F 17/50*    (2006.01)
   *G06T 19/20*    (2011.01)
   *G16H 50/50*    (2018.01)
   *A61B 5/11*     (2006.01)
   *G06T 13/40*    (2011.01)
   *A61F 2/46*     (2006.01)
   *A61B 34/10*    (2016.01)
   *G06F 19/00*    (2018.01)

(52) U.S. Cl.
   CPC ............ *A61B 5/4585* (2013.01); *A61B 34/10* (2016.02); *A61F 2/4657* (2013.01); *G06F 17/50* (2013.01); *G06F 19/00* (2013.01); *G06T 13/40* (2013.01); *G16H 50/50* (2018.01); *A61B 5/103* (2013.01); *A61B 2034/105* (2016.02); *A61F 2002/4668* (2013.01); *G06T 2210/41* (2013.01); *G06T 2219/2004* (2013.01); *G06T 2219/2016* (2013.01)

(56) References Cited

U.S. PATENT DOCUMENTS

2009/0264894 A1    10/2009  Wasielewski
2010/0042105 A1*    2/2010  Park ................. A61B 17/15
                                                        606/87
2011/0029116 A1     2/2011  Jordan et al.

OTHER PUBLICATIONS

Blankevoort et al., "Articular contact in a three-dimensional model of the knee", Journal of Biomechanics, vol. 24, No. 11, Jan. 1991, pp. 1019-1031.

International Search Report and Written Opinion to corresponding International Application No. PCT/EP/2011/072324, dated Aug. 17, 2012; 11 pages.

International Search Report and Written Opinion to corresponding International Application No. PCT/EP2011/072323, dated Sep. 4, 2012; 7 pages.

* cited by examiner

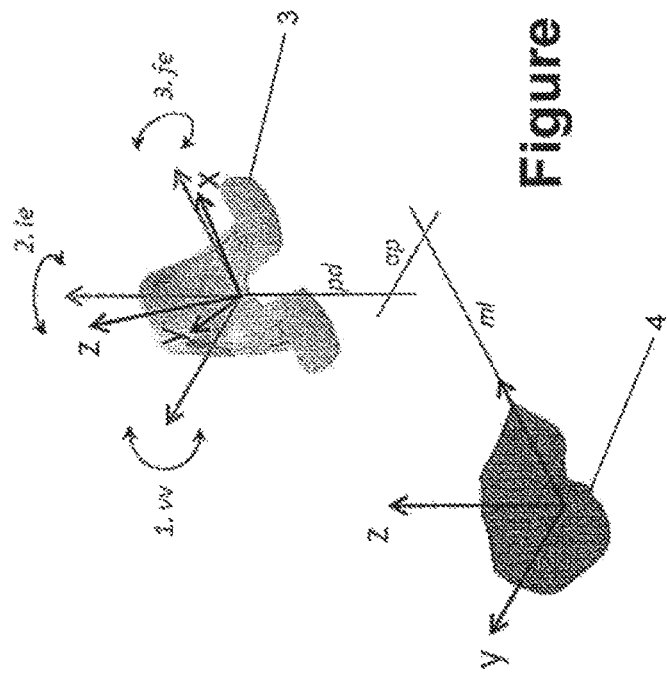
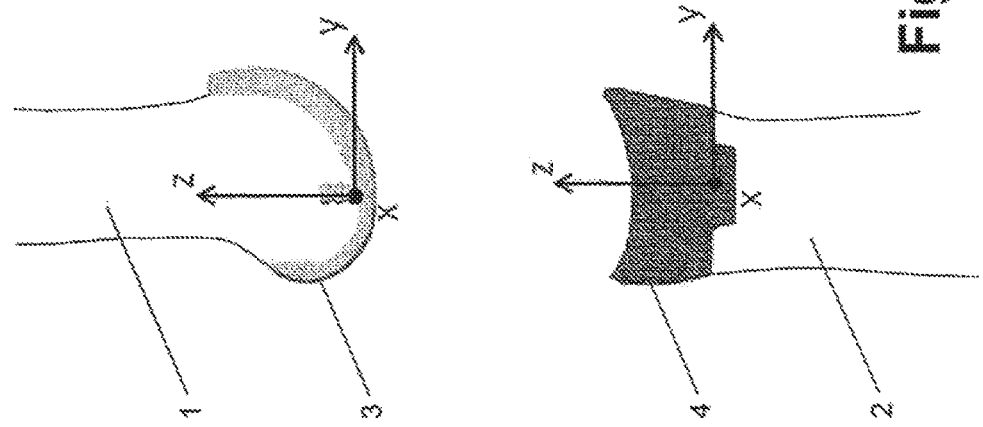
Figure 1a
Figure 1b

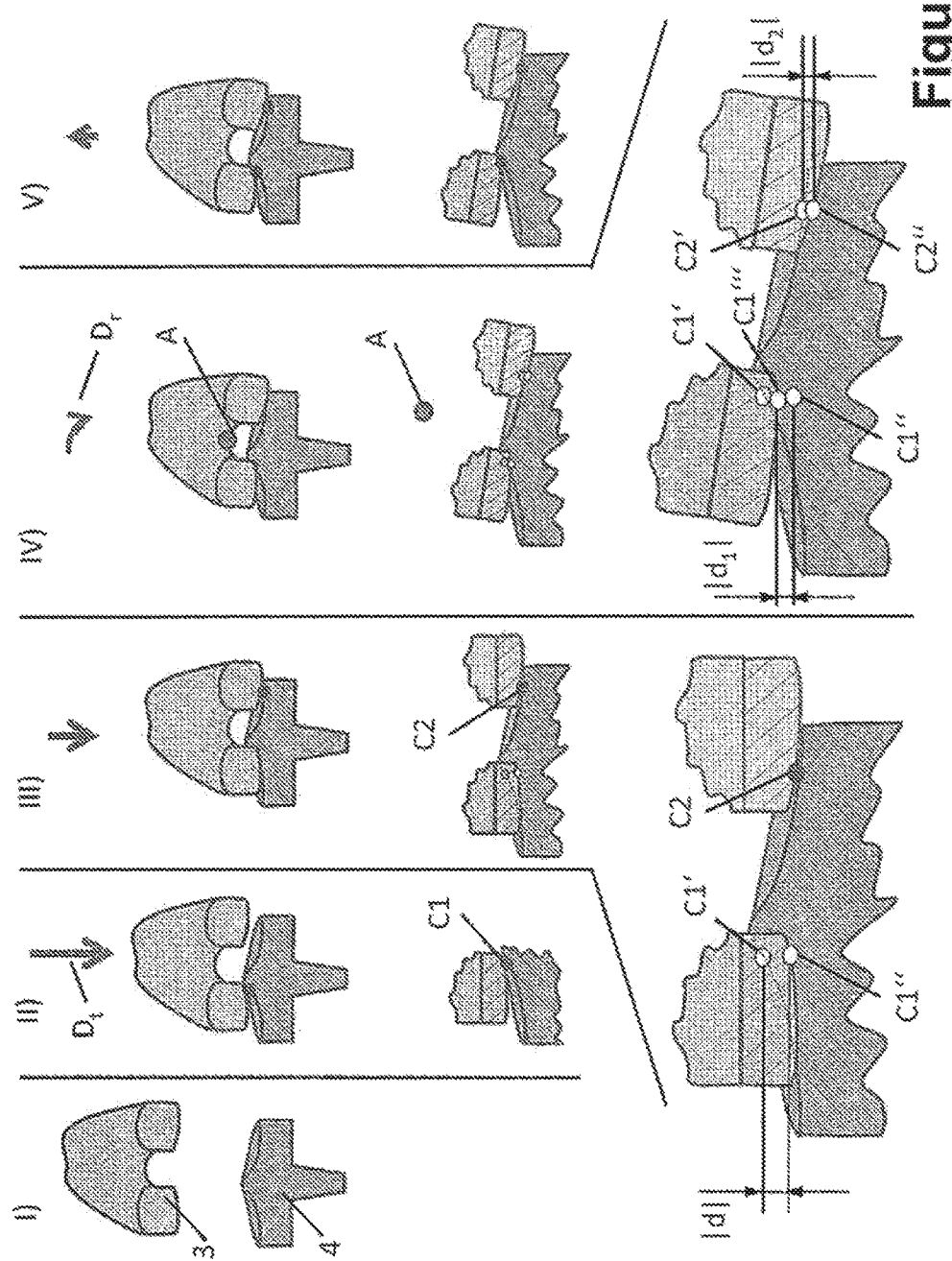

METHOD FOR DETERMINING CONTACT POSITION PARAMETERS OF A JOINT CONNECTING TWO BONES

RELATED APPLICATION DATA

This application is a continuation of U.S. patent application Ser. No. 14/362,988, filed on Aug. 20, 2014. U.S. patent application Ser. No. 14/362,988 is a national phase application of International Application No. PCT/EP2012/061757, which was filed Jun. 20, 2012 and published in the English language. The entireties of the aforementioned applications are herein incorporated by reference.

BACKGROUND

The present invention relates to a data processing method for determining six parameters of a contact position of a joint which connects two bones, a computer program implementing said method and a computer executing said computer program.

SUMMARY

In the human anatomy, two bones are typically connected via a joint which exhibits certain kinematic properties. The kinematic properties define a range of motion between the two bones. In other words, the joint typically supports a range of relative positions between the two bones. Such a relative position usually is a contact position in which the surfaces of the two bones are in contact with each other. In particular, there are two or three points of contact or a line contact between the two bones. In general, each contact position is defined by six parameters, wherein three parameters define a translational shift in three dimensions which are typically pairwise orthogonal. In a preferred example, the directions of the shifts are the proximodistal (pd) direction, the anterioposterior (ap) direction and the mediolateral (ml) direction. The other three parameters define a rotational shift or angular alignment, preferably about three pairwise orthogonal axes. Preferably, the three rotational parameters relate to the flexion/extension angle (fe), the internal/external angle (ie) and the varus/valgus angle (vv). In particular, the six parameters of a contact position describe the relative position between a first coordinate system of the first bone and a second coordinate system of the second bone.

The inventor has found that there are certain desired applications which require the six parameters of a contact position when a subset of the parameters of the contact position is given. An exemplary application is the visualization of the range of motion of the joint. The inventor has thus discovered the need to provide a method for determining the six parameters of a contact position of a joint which connects the two bones. Another application is to provide sample contact position datasets, each contact position dataset comprising the six parameters of a contact position, for example for performing an interpolation or extrapolation for determining parameters of a contact position from at least one of the sample contact position datasets.

The present invention thus relates to a data processing method for determining six parameters, corresponding to six degrees of freedom, of a contact position of a joint which connects two bones. One step of the method is acquiring a 3D model of each of the two bones. A 3D model is preferably represented by a model dataset, such as CAD data (computer aided design). The 3D model represents the shape of the bone. In particular, the 3D model represents the surface of the bone. Common types of 3D models include grid models or image datasets, wherein an image dataset represents a three-dimensional image of the bone. For example, each voxel of a 3D image dataset represents the density of the material located in the corresponding volume. It can thus be determined whether a voxel belongs to the bone or not. The 3D image data can be quantized, for example to two values, one value representing a voxel belonging to the bone and another value indicating the voxel as not belonging to the bone. A three-dimensional image dataset can for example be generated by three-dimensional imaging techniques such as CT, MRT or MRI. However, it lies in the scope of the present invention to use any suitable kind of 3D model.

In this document, the term "bone" can mean a complete bone or a part of the bone. However, a part or a complete bone can be replaced by an implant. The 3D model of a bone can thus represent a bone, a combination of a bone and an implant or an implant, or a part of any such object. The term "parameter" means a (numerical) value. The expressions "parameter" and "value of a parameter" are therefore used synonymously. However, the term "parameter" might also be used to identify a particular parameter out of the six parameters.

Another step of the method is acquiring four of the six parameters as given parameters. With these given parameters, the two missing parameters out of the six parameters of the contact position have to be determined. The two missing parameters are also referred to as remaining parameters.

Another step of the method is selecting initial values for the two remaining parameters. Preferably, the initial values for the remaining parameters are selected such that the 3D models of the bones are not in contact with each other. The combination of the four given parameters and the thus selected initial values of the two remaining parameters results in a relative position between the two 3D models such that they are not in contact with each other.

Preferably, the relative position between the two 3D models is defined by the relative position of coordinate systems assigned to the 3D models. Since the 3D models represent respective bones, these coordinate systems are equally assigned to the bones, such that the relative position of the coordinate systems also represents the relative position between the bones. Preferably, the coordinate systems associated with the 3D models (or bones) are defined such that the six parameters represent meaningful medical terms.

A further step of the method is varying the two remaining parameters virtually in order to achieve a virtual relative position between the two 3D models such that they are in contact with each other. This in particular means that there are two contact points between the two 3D models. Since the two 3D models represent the bones, this means that the two bones are also in contact if they are in the same relative position as the two 3D models. With at least two contact points, there is a defined contact position between the 3D models and therefore between the bones. There can of course be more than two contact points or there could be another kind of contact, such as a line contact or an area contact.

A contact point is a common point on the surfaces of both 3D models (or bones) in which the surfaces touch, but do not intersect each other. This reflects the physical property that a bone cannot penetrate into another bone. However, in the virtual space, there can be a relative position between the 3D models such that one model penetrates into the other. In this case, there is at least one point in space which lies on the surfaces of both 3D models. However, such a point is not considered as a contact point. In other words, a contact point (which could also be a contact area) is a point in space which lies on the surfaces of both 3D models, while neighbouring points to the contact point on the surface of one 3D model exhibit a distance to corresponding neighbouring points to the contact point on the surface of the other 3D model.

In yet other words, there is a gap between the surfaces of the two 3D models around the contact point.

Preferably, the (first and second) contact points are determined with respect to the surface of one of the two 3D models. In other words, these two contact points are given in a coordinate system assigned to this 3D model.

In one embodiment of the present invention, the two remaining parameters are one translational parameter and one rotational parameter. Preferably, the axis of rotation of the remaining rotational parameter is perpendicular to the direction of the remaining translational parameter.

In this embodiment, one possible implementation for varying the two remaining parameters comprises, starting from the initial values of the remaining parameters, moving the 3D models virtually towards each other along the direction of the remaining translational parameter (also referred to as approach direction) until there is a first contact point between the surfaces of the two 3D models. This movement is continued until there is a second contact point between the surfaces of the 3D models. In this stage, the two 3D models intersect each other. As outlined above, points lying on the intersection line between the two 3D models are not considered as a contact point. When the second contact point is reached, the remaining rotational parameter is then calculated such that the two 3D models of the two bones are in contact at two contact points. The remaining translational parameter is adapted appropriately if required, in particular if the second contact point does not lie on the axis of rotation of the remaining rotational parameter.

Preferably, in the last step described above, the remaining rotational parameter is changed such that the difference of the distances, by which the first contact point and the second contact point are moved by changing the remaining rotational parameter, in the direction of the remaining translational parameter equals the distance by which the 3D models are moved virtually towards each other along the direction of the remaining translational parameter between reaching the first contact point and the second contact point, and the remaining translational parameter is amended by the distance the second contact point has moved in the direction of the remaining translational parameter by changing the remaining rotational parameter. The amendment is made in the direction against the movement of the second point. If changing the rotational parameter for example results in a movement of the second contact point in the direction of the remaining translational parameter, then the remaining translational parameter is amended such that the second contact point, and therefore also the first contact point, moves in a direction opposite to the direction of the remaining translational parameter in order to compensate for that. The difference of the distances is calculated by subtracting the distance, by which the first contact point has moved by changing the remaining rotational parameter, from the distance by which the second point has travelled at the same time. If a movement is not parallel to the direction of the remaining translational parameter, then the distance is considered to be the projected portion of the movement that is parallel to the direction of the remaining translational parameter.

If the remaining rotational parameter is changed, each contact point moves towards or away from the surface of the other 3D model, depending on the location of the axis of rotation of the remaining rotational parameter. The amounts (absolute values) of these movements depend on the distances of the contact points from the axis of rotation of the remaining rotational parameter. In other words, amending the remaining rotational parameter causes translational shifts of the two contact position in the approach direction. A distance (or shift) can be positive or negative. A positive distance relates to a movement in the direction of the remaining translational parameter, while a negative distance relates to a movement against the direction of the remaining translational parameter.

Depending on the angle by which the remaining rotational parameter is changed and/or the structure of the surface of the 3D models, a situation might occur in which, after the procedure described above, the two contact points do not lie on the surface of the other 3D model. As an option, the process of varying the two remaining parameters is iteratively repeated, with the value which was determined in the preceding iteration being selected as the initial value of the remaining rotational parameter. The direction in which the remaining rotational parameter is amended can of course be determined individually in each iteration. Preferably, the initial value of the remaining translational parameter is the same as the initial value of the remaining translational parameter in the previous iteration. However, the initial value of the remaining translational parameter can be chosen based on the value of this parameter determined in the previous step. In particular, the value determined in the previous step is changed by a default value, in particular by the distance between the first and second contact points, as determined in the previous step, in the direction of the remaining translational parameter such that the two 3D models are moved away from each other before the next iteration starts.

Preferably, when the 3D models of the bones touch over an area and not over a single contact point, the center of this contact area is chosen as the contact point. In particular, the center is determined as the centroid of the area.

One application of the method described in this document is to compute and/or visualize the range of motion of the joint. In this case, a group or sequence of one or more of the given parameters is selected so as to represent a particular motion of the joint, while the other given parameters are kept constant. The two remaining parameters are then determined as described, for example on the fly. A sequence of datasets representing the given parameters thus leads to a sequence of datasets representing the six parameters of contact positions.

In another embodiment, a plurality of parameter sets is defined for the four given parameters and a contact position is determined for each of the parameter sets. This results in a plurality of contact position datasets, each dataset comprising six parameters, which can, for example, be used as sample contact position datasets for interpolating or extrapolating contact positions as described in document PCT/EP2011/072323. The plurality of contact position datasets represents the kinematic footprint of the joint, and in particular of the implant.

Preferably, each given parameter in the parameter sets is varied in steps within a given range. Further preferably, the given parameters are varied in equidistant steps.

According to one embodiment of the present invention, collision detection techniques are used to determine whether or not there is a contact point between the surfaces of the 3D models. In particular, the collision detection technique is selected depending on the kind of 3D models. In a collision detection technique, it is determined whether or not two objects, which means two bones or 3D models within this document, collide, or in other words are in contact with each other. Preferably, collision detection makes use of distance maps. A distance map comprises, for a mesh of points in space, the distance to the surface of an object. A distance map is preferably pre-calculated for the particular object.

The method described in some of the above embodiments calculates two contact points between the two 3D models. In an alternative embodiment, such an accurate calculation of a contact point is not required. The two 3D models are considered as being in contact with each other if the remaining rotational parameter and the remaining translational parameter are being adjusted in such way that the minimum possible distance between the two 3D models in the direction of the remaining translational parameter is minimised. Preferably, the distance is the distance between a reference point defined with respect to one of the 3D models and a plane running through the other 3D model. Preferably, this plane is perpendicular to the direction of the remaining translational parameter. The minimum possible distance is given if the two 3D models cannot further approach each other without intersecting each other.

For each particular value of the remaining rotational parameter, there is a relative position resulting in the minimum possible distance for this particular value. If this relative position has just one contact point between the two 3D models, then a rotation about the axis of rotation of the remaining rotational parameter leads to another relative position for which the minimum possible distance is smaller. When this rotation is continued, there will occur a relative position which results in two contact points between the two 3D models. When the rotation is then further continued, the minimum possible distance starts to rise again. In other words, the curve of the minimum possible distance over the remaining rotational parameter must have a minimum. The relative position corresponding to this minimum is considered to represent the desired contact position.

The reference point defined with respect to the one of the 3D models should be far enough away from its surface to ensure that the minimum in the curve corresponds to the contact position.

In one particular embodiment, the minimum possible distance is not calculated exactly, but is approximated. The distance between the two 3D models is reduced step-wise until they intersect with each other. The minimum possible distance must then lie between the distance of the current step and the distance of the previous step. For example, the middle between these two distances is used as the minimum possible distance. It is also possible to iteratively perform a search in the range defined by these two distances, for example using an interval bisection approach.

In a particular embodiment, the value of the remaining rotational parameter for which the minimum possible distance is minimised is calculated by performing the following steps:
(a) defining a range of values for the remaining rotational parameter;
(b) calculating a first value lying in the middle of the range of values;
(c) calculating a second value lying in the middle between the lower boundary of the range of values and the first value;
(d) calculating a third value lying in the middle between the upper boundary of the range of values and the first value;
(e) determining a first minimum possible distance for the first value of the remaining rotational parameter, a second minimum possible distance for the second value of the remaining rotational parameter and a third minimum possible distance for the third value of the remaining rotational parameter;
(f) repeating steps (b) to (e) for a predetermined number of iterations with a new range of values, the new range of values having half the width of the current range of values and being centered about the one of the first, second or third values which results in the smallest of the first, second and third minimum possible distances; and
(g) selecting the one of the first, second or third values which results in the smallest of the first, second and third minimum possible distance for the remaining rotational parameter.

This embodiment implements an iterative search. The range defined in step (a) is an initial range of values in the first iteration and might represent a range which equals or is slightly larger than the anatomically possible range of the corresponding movement. In step (b), this range is bisected, resulting in two half ranges. The first value marks the centre of the range of values. In steps (c) and (d), the centre of each of the half ranges is determined, such that the second and third values mark the centres of these half ranges.

In step (e), respective minimum possible distances are calculated for the first, second and third value. These distances are used to determine the reduced range of values for the next iteration. In particular, the one of the first, second and third values corresponding to the smallest one of the first, second and third minimum possible distances defines the direction for the subsequent search.

In step (f), the range of values is determined for the next iteration. If the first minimum possible distance is the smallest of the three minimum possible distances, then the new range of values is limited by the second and third value. In other words, the central half of the range of values is used as the next range of values. If the second minimum possible distance is the smallest of the three minimum possible distances, then the new range of values is limited by the current lower limit of the range of values and first value. In other words, the lower half of the range of values is used as the next range of values. If the third minimum possible distance is the smallest of the three minimum possible distances, then the new range of values is limited by the first value and the current upper limit of the range of values. In other words, the upper half of the range of values is used as the next range of values.

It shall be noted that not all three minimum possible distances have to be calculated in each of the iterations. The smallest minimum possible distance in a particular iteration can be re-used as the first minimum possible distance in the subsequent iteration.

Once the predetermined number of iterations has been performed, a value of the remaining rotational parameter which is considered as corresponding to the minimized minimum possible distance, and thus as corresponding to the contact position, is determined. For example, the one of the first, second and third values corresponding to the smallest minimum possible distance in the last iteration is selected as the remaining rotational parameter.

A further aspect of the present invention relates to storing the six parameters of a contact position, and in particular to storing the parameters for a plurality of contact positions. The parameters are preferably stored in a list, such as in a text file. Each line of the list or the text file comprises the six parameters for a particular contact position. The lines are preferably consecutively numbered, wherein the number is the first data item in a line and is followed by the parameters. The parameters are preferably comprised in all lines in the same order. Further preferably, there is an identifier for the parameter, followed by an equal sign and the value of the respective parameter. There can be a space between the identifier and the equal sign and/or between the equal sign and the value of the parameter or not. The value of a parameter can be truncated to a predefined number of decimal places, such as for example 2, 3, 4, 5 or more decimal places.

The method in accordance with the invention is in particular a data processing method. The data processing method is preferably performed using technical means, in particular a computer. In particular, the data processing method is executed by or on the computer. The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term of computer encompasses a cloud computer, in particular a cloud server. The term of cloud computer encompasses cloud computer system in particular comprises a system of at least one cloud computer, in particular plural operatively interconnected cloud computers such as a server farm. Preferably, the cloud computer is connected to a wide area network such as the world wide web (WWW). Such a cloud computer is located in a so-called cloud of computers which are all connected to the world wide web. Such an infrastructure is used for cloud computing which describes computation, software, data access and storage services that do not require end-user knowledge of physical location and configuration of the computer that delivers a specific service. In particular, the term "cloud" is used as a metaphor for the internet (world wide web). In particular, the cloud provides computing infrastructure as a service (IaaS). The cloud computer may function as a virtual host for an operating system and/or data processing application which is used for executing the inventive method. Preferably, the cloud computer is an elastic compute cloud (EC2). A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step, an input device or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information".

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit—CPU) which executes the computer program elements and optionally a volatile memory (in particular, a random access memory—RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. Preferably, the data storage medium is a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The invention further relates to a computer on which said program is running or into the memory of which the program is loaded.

Different features and/or embodiments described in this document can be combined in accordance with the invention as long as technically sensible and feasible. In particular, one or more features of two or more embodiments can be combined with each other. In particular, a feature of one embodiment which has the same or similar function of another feature of another embodiment can be exchanged. In particular, a feature of one embodiment which supplements a further function to another embodiment can be added to the other embodiment.

BRIEF DESCRIPTION OF THE FIGURES

The invention shall now be explained in more detail with reference to the accompanying figures. The figures show:

FIG. 1a illustrates two components of an artificial knee joint in a side view,

FIG. 1b illustrates the components of FIG. 1a in a perspective view,

FIGS. 3a and 3b illustrate an approach for determining the remaining parameters.

DETAILED DESCRIPTION

Figure 2B:
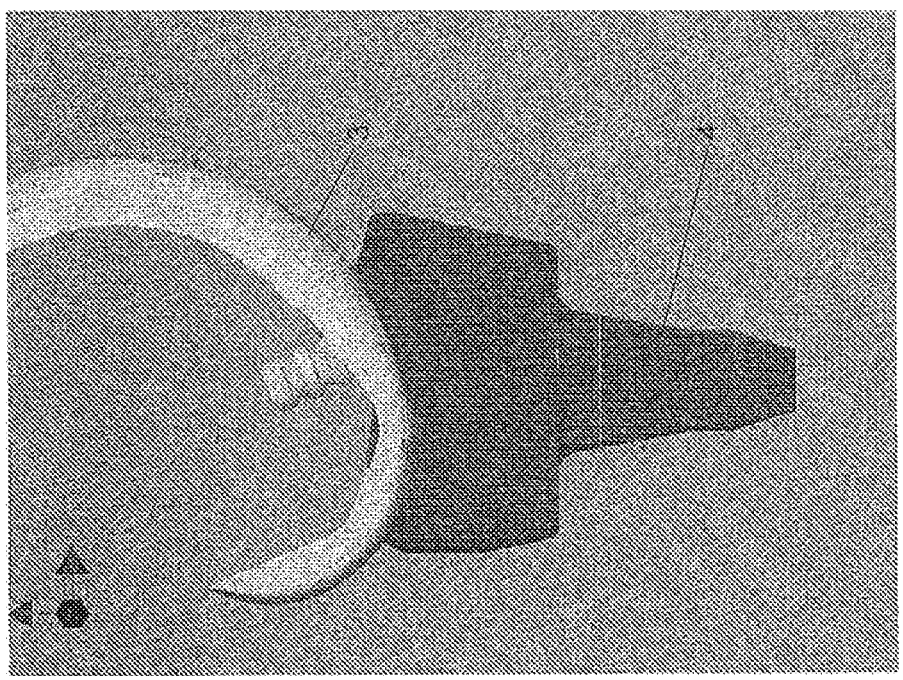
FIG. 2b illustrates a second contact position.

FIG. 1a schematically shows a side sectional view of a femur 1 as first bone and a tibia 2 as a second bone. A femur implant 3 is attached to the femur 1 and a tibia implant 4 is attached to the tibia 2. The femur implant 3 and the tibia implant 4 constitute an artificial knee joint. As can be seen from FIG. 1a, a coordinate system is defined for each implant, and thus for each bone. It is to be noted that attaching an implant to a bone is not a part of the present invention which only relates to the analysis of a joint.

FIG. 1b shows a perspective view of the implants 3 and 4. Next to the coordinate systems attached to the implants, the six parameters which define the relative position between the coordinate systems, and therefore between the implants 3 and 4 or the bones 1 and 2, are indicated. Three of the six parameters represent translational shifts in the proximodistal (pd), anteroposterior (ap) and mediolateral (ml) directions. The other three of the six parameters correspond to rotations about certain axes representing a flexion/extension (fe or flex) angle, an internal/external (ie) angle and a varus/valgus (vv) angle, respectively. Preferably, the coordinate systems associated with the implants are arranged such that the six parameters represent meaningful medical terms. A contact position is a relative position between the coordinate systems of the implants such that the bones (or implants) are in contact.

Figure 8:
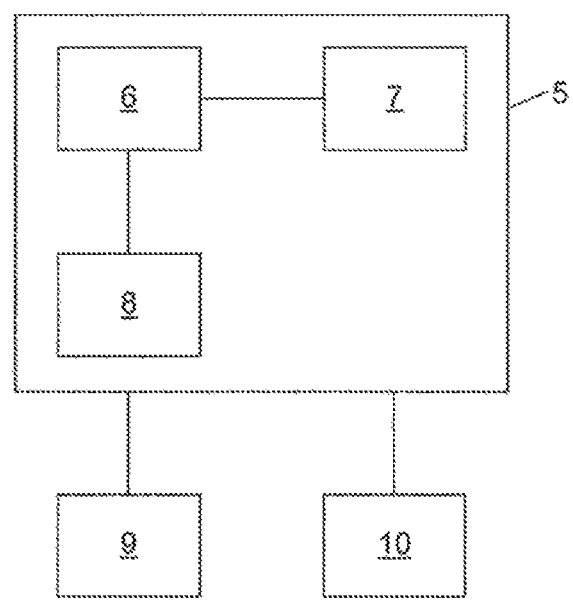
FIG. 8 illustrates a schematic structure of an apparatus for carrying out the method.

FIG. 8 shows a computer 5 for carrying out the method according to the present invention. The computer 5 comprises a central processing unit 6 connected to a memory 7 and an interface 8. Connected to the computer 5 is an input device 9 and a display device 10. In the present example, the input device 9 is a mouse or a keyboard. The memory 7 stores data and provides the data to the central processing unit 6. Additional data can be acquired or data can be provided by the interface 8.

It shall be noted that, in this document, an implant is considered as a part of a bone. So the femur plant 3 is considered as a part of the femur 1 and the tibia implant 4 is considered as a part of the tibia 2. In the present invention, 3D models of bones are used. It is sufficient if these models represent the surfaces of the bones which can get in contact with each other in order to constitute a contact position. It can thus be sufficient to use 3D models of the femur implant 3 and the tibia implant 4. In the exemplary embodiment described in the following, 3D models of the two implants 3 and 4 are used. However, the invention is not limited to this example. So the 3D models might represent just a bone or at least parts of a combination of a bone and an implant. In addition, the invention is not limited to a joint between a femur and a tibia as used in the present example.

Figure 2A:
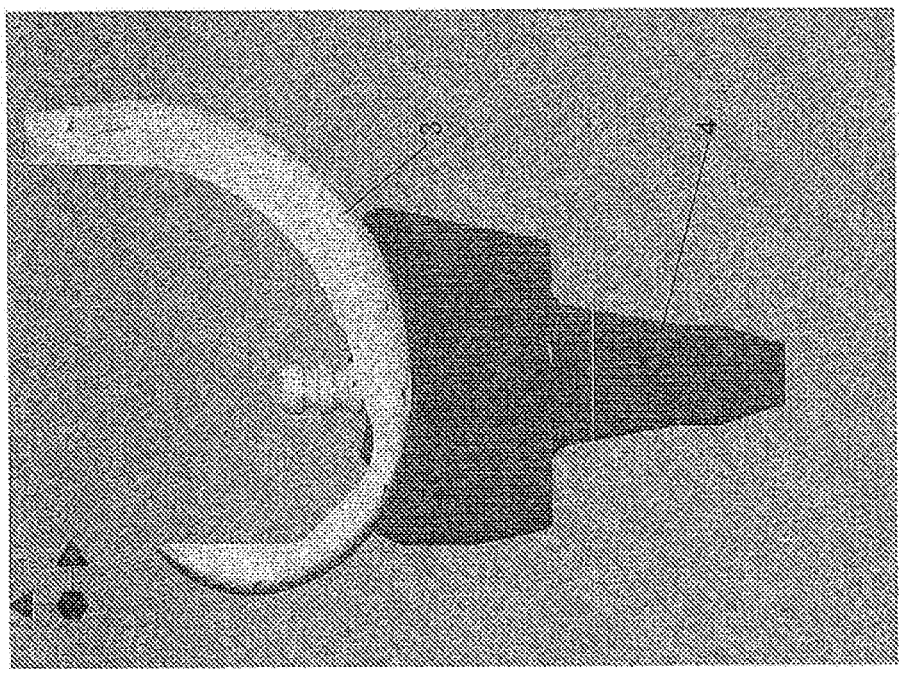
FIG. 2a illustrates a first contact position.

FIGS. 2a and 2b show two exemplary contact positions between the femur implant 3 and the tibia implant 4. For both contact positions, the parameters ie, fe, ap and ml were given and the remaining parameters vv and pd have been determined according to the present invention. The difference between the contact positions in FIGS. 2a and 2b is that different values for the parameter fe have been given.

In its upper part, FIG. 3a shows five different stages (denoted I, II, III, IV, V) in the process of determining the two remaining parameters pd and vv. In particular, a frontal view of the femur implant 3 and the tibia implant 4 is shown. The first to fifth stages are shown from left to right. The middle part of FIG. 3a shows sectional views of the implants in the second to fifth stage. The bottom part of FIG. 3a shows more detailed views of the contact points in the third and fourth stage.

In the first stage, the relative position between the femur implant 3 and the tibia implant 4 is defined by the four given parameters ie, fe, ap and ml as well as initial values for the two remaining parameters pd and vv. The remaining rotational parameter is vv and the remaining translational parameter is pd. For example, the initial values are pd=100 mm and/or vv=0°.

In the second stage, the 3D model of the femur implant 3 is moved towards the tibia implant 4 along the direction $D_t$ of the remaining translational parameter pd until the two 3D models are in touch with each other at a first contact point C1. In this relative position, the first contact point C1 lies on the surfaces of both 3D models. In the following, the first contact point C1 is defined on the surface of a 3D model of the femur implant 3 and is located in femur space. The corresponding point on the surface of the tibia implant 4 is located in tibia space and is called C1'.

In the third stage, the movement performed in the second stage is continued until there is a second contact point C2 between the two 3D models. In this stage, the contact point C1 on the surface of the 3D model of the femur implant 3 moves into the 3D model of the tibia implant 4 with a corresponding point C1" located in tibia space. In the following, the second contact point C2 is defined on the surface of a 3D model of the femur implant 3 and is located in femur space. The corresponding point on the surface of the tibia implant 4 is located in tibia space and is called C2'.

In the third stage of the present example, the femur implant 3 has been moved virtually towards the tibia implant 4 along the approach direction $D_t$ by a distance d, which means that, for the relative position between the two implants as shown in the third stage in FIG. 3a, the distance between the points C1' and C1" is also d.

In the fourth stage, the remaining rotational parameter vv is calculated. In particular, the change of the remaining rotational parameter is formed about the axis of rotation A, resulting in a rotation as indicated by the arrow $D_r$. The femur implant 3 is rotated by an angle such that the second contact point with location C2' in tibia space moves to a location C2", while the first contact point with location C1" in tibia space moves to a location C1''' in the opposite direction $-D_t$.

The femur implant 3 is rotated by an angle in a rotational direction $D_r$ representing the remaining rotational parameter vv such that the second contact point C2 moves into the direction $D_t$ by a distance $d_2$, while the first contact point C1 moves in the opposite direction $-D_t$ by a distance $d_1$ such that $d_2-d_1=d$. Note that the difference is calculated by subtracting $d_1$ from $d_2$, with $d_1$ aiming in opposite direction of $D_t$. Therefore $d_1$ will have a negative value while $d_2$ will have a positive value.

In a fifth stage, the femur implant 3 is moved in the direction $-D_t$ by the distance $-d_2$ (with negative value), such that both contact points C1 and C2 now also lie on the surface of the 3D model of the tibia implant 4. The relative position between the femur implant 3 and the tibia implant 4 is then a contact position.

Figure 3B:
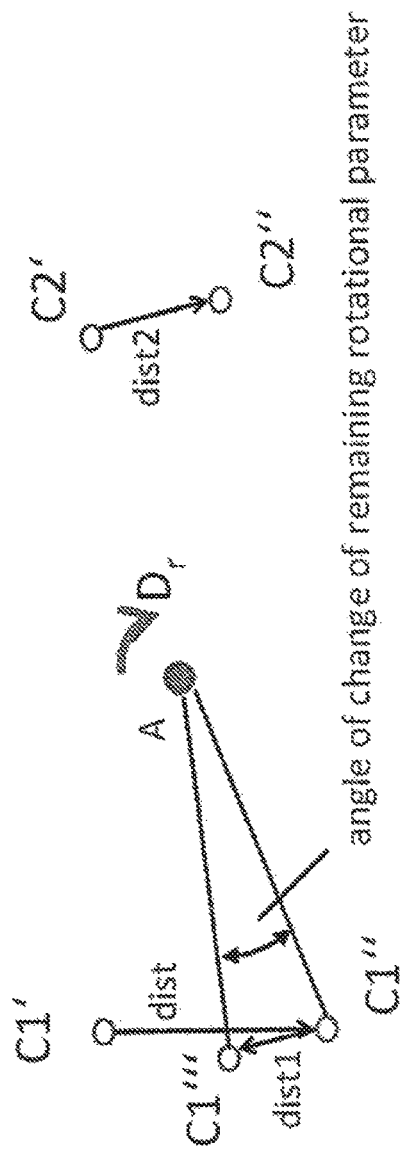
Figure 3B:
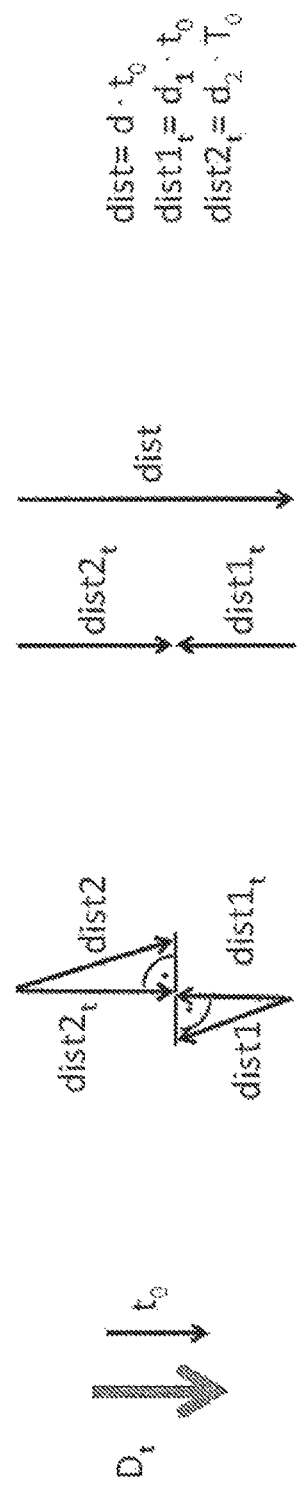

FIG. 3b shows the movements of the contact points for the third and fourth stages in vector representation. The movement of the third stage is shown as vector dist which has the associated distance d as a scalar representation. In the context of this application, a positive sign of a distance reflects that the distance is travelled along $D_t$ and a negative sign reflects that it is travelled in the opposite direction. In general, the movements of the contact points are not fully parallel to $D_t$ and have also a perpendicular portion. Therefore the movements from the third and fourth stages are represented as vectors dist1 for the first contact point and dist2 for the second contact point, with their parallel portions $dist1_t$ and $dist2_t$. The unity vector $t_0$ with length 1 has the same direction as $D_t$. The vector $dist1_t$ can be expressed as the unity vector $t_0$ multiplied by the distance scalar d1, the vector $dist2_t$ can be expressed as the unity vector $t_0$ multiplied by the distance scalar d2 and the vector dist can be expressed as the unity vector $t_0$ multiplied by the distance scalar d.

It shall be noted that the rotation about the axis A does not only cause a shift in the direction $D_t$ corresponding to the parameter pd, but also a shift in the direction ml (the left-right-direction in FIG. 3b). Depending on the surfaces of the implants 3 and 4, the contact points C1 and C2 may not lie on the surface of the 3D model of the tibia implant 4 at the end of stage 5. The process of FIG. 3a might therefore be repeated, wherein the initial value of the parameter vv is selected as the value which was determined at the end of the fifth stage.

The process of determining the six parameters of a contact position can be performed repeatedly for different sets of given parameters in order to obtain a set of contact positions. This set of contact positions can then for example be provided to other applications. Preferably, the values of the given parameters in the plurality of sets are varied systematically. This approach is schematically shown in FIG. 4.

Figure 4:
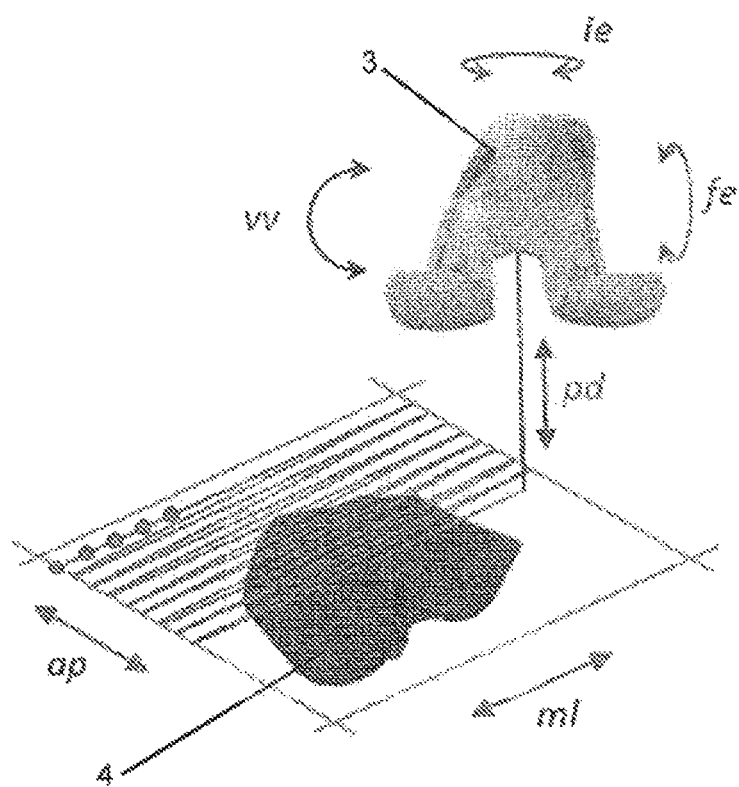
FIG. 4 illustrates an approach for determining a plurality of contact positions.

FIG. 4 shows a raster scan over a plane defined by the parameters ap and ml. In particular, the parameters ie and fe are kept constant and a value for the parameter ap is selected. Then, the parameter ml is continuously increased from a starting value and thus covers a range of values, preferably in equidistant steps. Then, the value of the parameter ap is amended, preferably by a step of a predetermined width. Then, the value of the parameter ml runs through the range again, either in the same direction or in a direction reverse to the one for the previous value of the parameter ap as shown in FIG. 4. The value of the parameter ap is also amended over a given range. The plane formed by the two value ranges for the parameters ap and ml is therefore systematically gone over. Two higher-ranking loops can be implemented for the other given parameters ie and fe.

Figure 5:
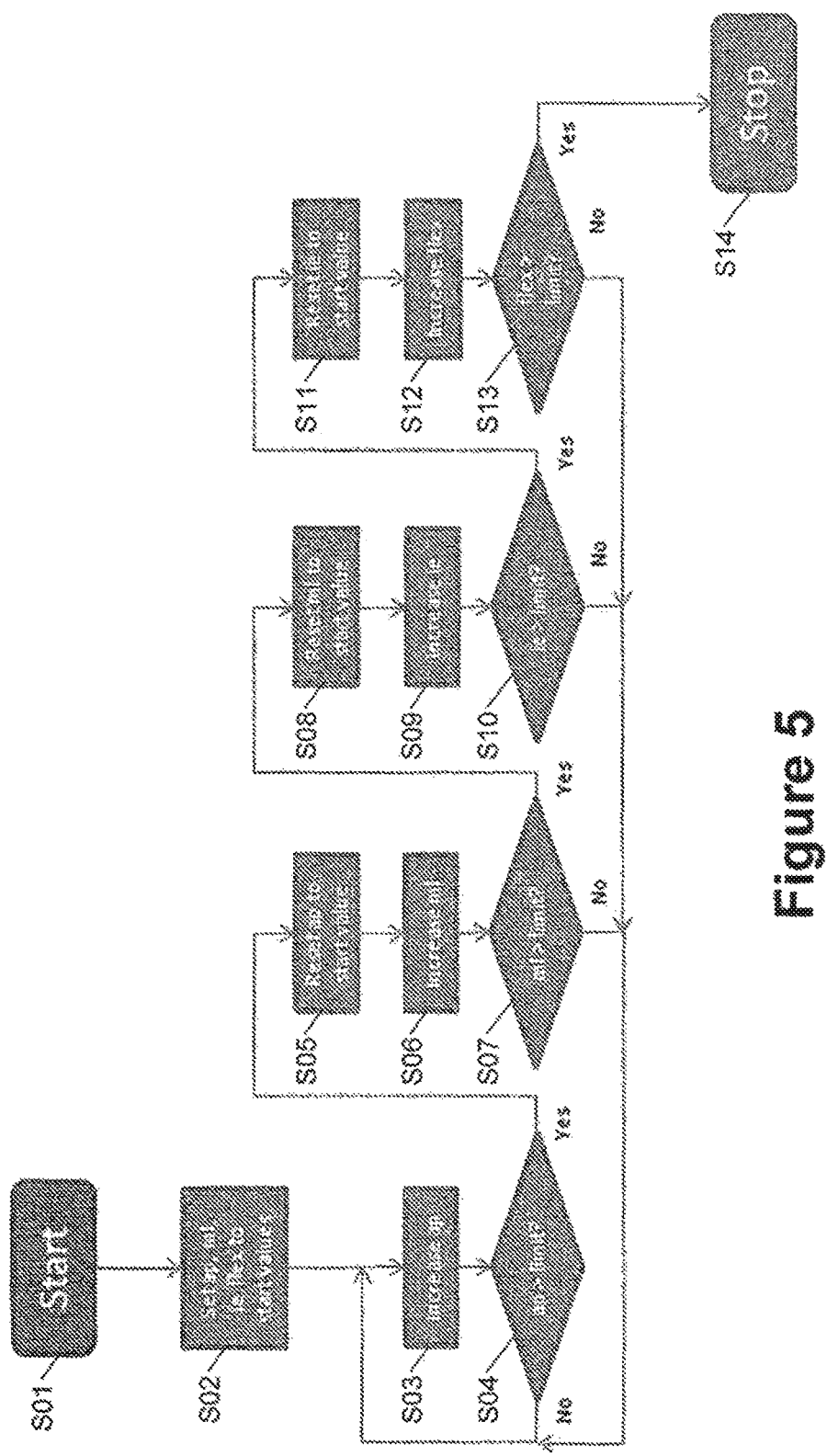
FIG. 5 illustrates a flow diagram for the approach of FIG. 4.

A flow diagram for systematically varying the values of the given parameters is shown in FIG. 5. In step S01 the process starts. In step S02, start values for the given parameters ap, ml, ie and flex are set. In step S03, the remaining parameters pd and vv are determined as described above and then the value of the given parameter ap is increased. In step S04, it is determined whether or not the value of the parameter ap is above a predetermined limit. If this is not the case, then the process returns to step S03 in order to loop over a range of ap values. If the increased value of the parameter ap is above the limit, then the process branches to step S05 where the value of the parameter ap is reset to the start value. The process then continues with step S06 in which the remaining parameters are determined as described above and the value of the given parameter ml is increased. In the following step S07, it is determined whether or not the value of the parameter ml is above a limit. If this is not the case, then the process branches to step S03.

If the value of the parameter ml is above the limit, the process continues with step S08 where the value of the parameter ml is reset to the start value. In the following step S09, the remaining parameters are determined as described above and the value of the parameter ie is increased. Then, in step S10, it is determined whether or not the value of the parameter ie is above a predetermined limit. If this is not the case, then the process branches to step S03.

If the value of the parameter ie is above the limit, then the process continues with step S11, in which the value of the parameter ie is reset to its start value. In the following step S12, the remaining parameters are determined as described above and the value of the parameter flex is increased. In step S13, it is then determined whether or not the value of the parameter flex is above a predetermined limit. If this is not the case, then the process branches to step S03. If the value of the parameter flex is above the limit, then the process continues with step S14 where the process is stopped.

With this approach, sets of given parameters are created by running through four nested loops. In steps S03, S06, S09 and S12, the respective parameters are preferably increased in predefined steps, which means that the values for each given parameter are distributed equidistantly. It is of course possible to change the order of the loops such that the four-dimensional given parameter space is run through along a different path. In addition, the parameters in the loops can be other parameters than ap, ml, ie and flex if other parameters than vv and pd are the remaining parameters.

As described above, FIG. 8 shows a computer 5 for carrying out the method. The computer 5 acquires the 3D models of the bones preferably via the interface 8, for example from a hard disc or over a network. The 3D models are stored in the memory 7. The memory 7 preferably also stores the given parameters or sets of given parameters, which can also be acquired via the interface 8 or from the input device 9. The central processing unit 6 uses the 3D models and the given parameters to determine the remaining parameters as described above. The result, that is the remaining parameters or all six parameters of the contact position can be stored in the memory 7, sent over the interface 8, output on the display device 10 or a combination thereof. It further possible to calculate a transformation matrix from the six parameters. The transformation matrix also describes the relation between the two coordinate systems assigned to the bones 1 and 2 or the implants 3 and 4.

Figure 6:
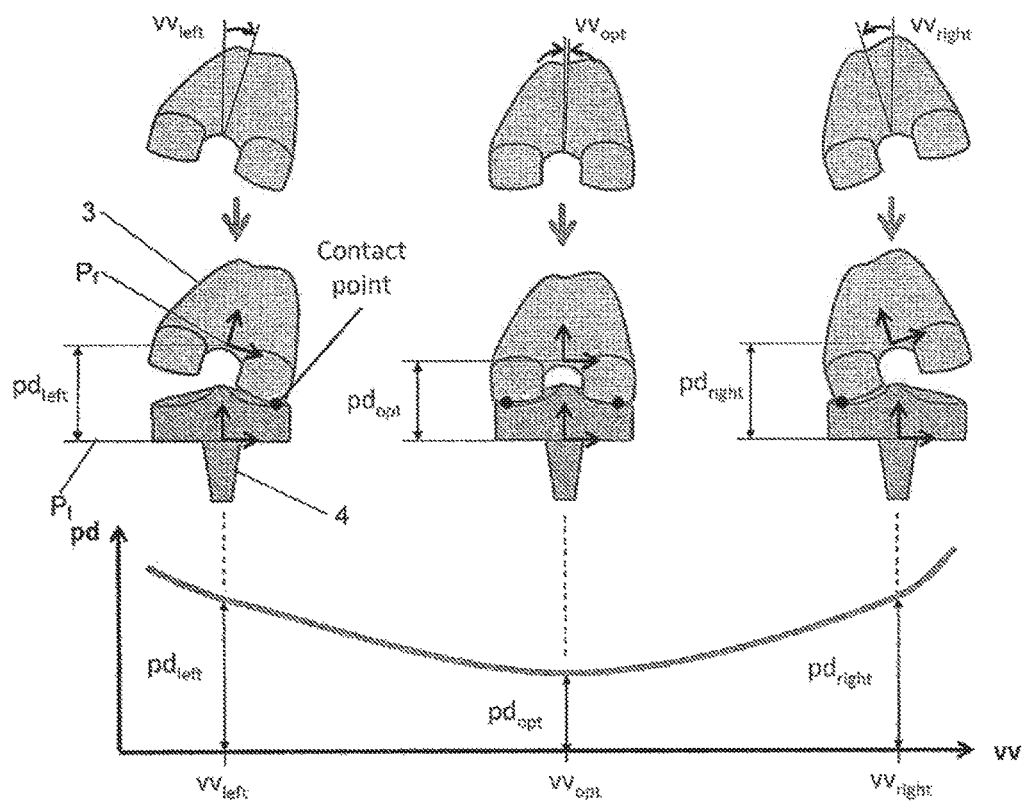
FIG. 6 illustrates another approach for determining the remaining parameters.

FIG. 6 illustrates an alternative approach for determining the remaining parameters. A reference point $P_f$ is defined for the femur implant 3 and a reference plane $P_t$ is defined for the tibia implant 4. In the figure, three different virtual relative positions between the femur implant 3 and the tibia implant 4 are shown for different values of the parameter vv. In each virtual relative position, the femur implant 3 is in touch with the tibia implant 4 in at least one point. The distance between the two implants is defined as the distance between the reference point $P_f$ and the reference plane $P_t$.

The minimum possible distance for each value of vv occurs when the two implants 3 and 4 are in touch with each other in two points.

As can be seen in FIG. 6, the virtual relative positions on the left and on the right for the values $vv_{left}$ and $vv_{right}$ of the remaining rotational parameter each have only one contact point between the femur implant 3 and the tibia implant 4. The corresponding minimum possible distances $pd_{left}$ and $pd_{right}$ are larger than the minimum possible distance $pd_{opt}$ for the value $vv_{opt}$ of the remaining rotational parameter which occurs when the implants have two contact points as shown in the central relative position. The graph of the minimum possible distance over the remaining rotational parameter vv therefore has a minimum which has to be found, because it corresponds to a stable contact position.

Figure 7A:
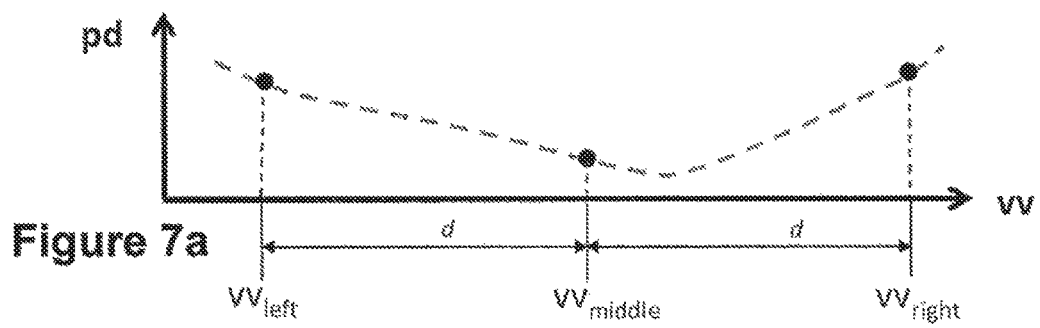
FIGS. 7a, 7b, 7c, 7d, 7e, 7f, and 7g illustrate an example for the approach of FIG. 6.
Figure 7B:
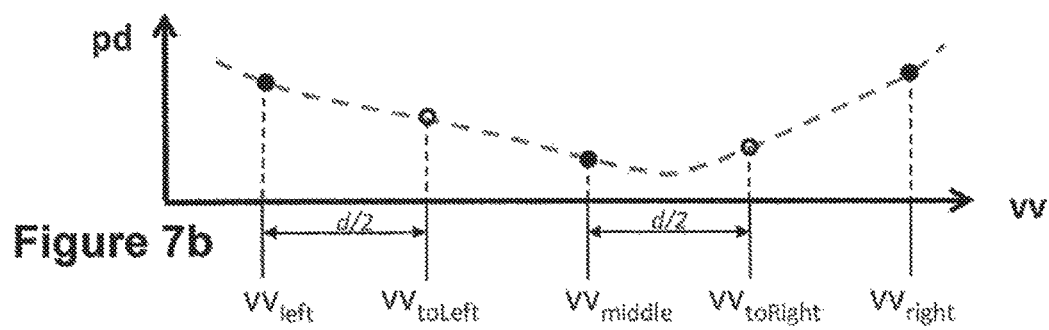

An exemplary search approach is shown in FIGS. 7a, 7b, 7c, 7d, 7e, 7f, and 7g. Two values $vv_{left}$ and $vv_{right}$ are defined to limit the range of vv being searched as shown in FIG. 7a. In the middle between both values, a first value for $vv_{middle}$ is calculated. Then a value $vv_{toLeft}$ is calculated in the middle between $vv_{left}$ and $vv_{middle}$. In analogy, a value $vv_{toRight}$ is calculated in the middle between $vv_{middle}$ and $vv_{right}$. This is shown in FIG. 7b.

Figure 7C:
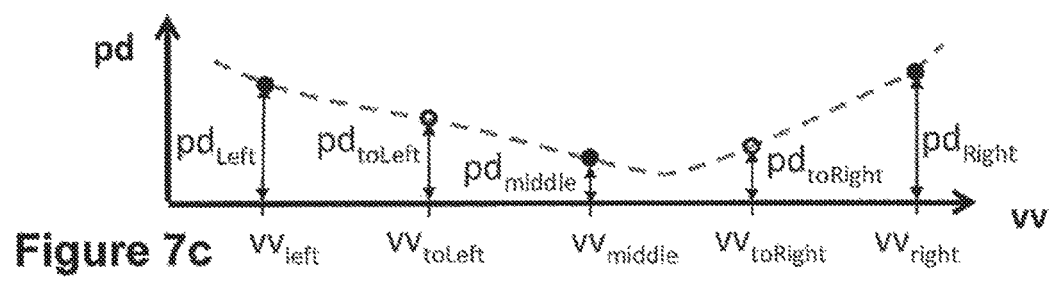
Figure 7D:
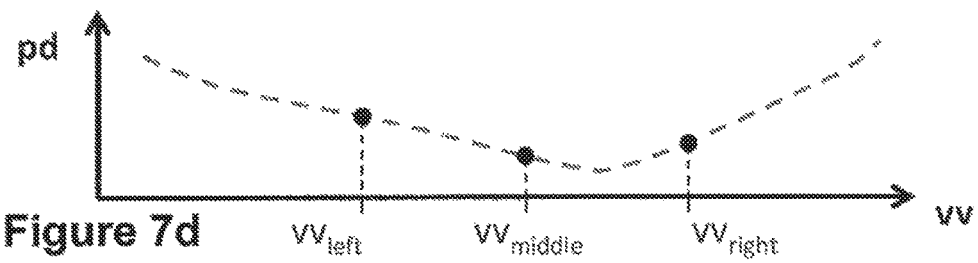

For each of $vv_{middle}$, $vv_{toLeft}$ and $vv_{toRight}$, a dedicated contact search is conducted in pd direction to find the minimum possible distances $pd_{middle}$, $pd_{toLeft}$ and $pd_{toRight}$ that establish touching surface contact between the implants 3 and 4. The contact condition is being detected using collision techniques, e.g. based on grid models. For this purpose, the distance may be changed by a suited iterative or other systematic approach and each virtual relative position resulting from the distance pd, vv and the other remaining fixed parameters ml, ap, flex, ie will be checked for contact until the component surfaces touch. The resulting minimum possible distances are shown in FIG. 7c.

In a next step, it is determined which of the calculated minimum possible distances $pd_{middle}$, $pd_{toLeft}$ and $pd_{toRight}$ is the smallest in order to define a new range for vv in the next iteration.

In case $pd_{toLeft}$ is smaller than $pd_{middle}$, the minimum of the graph is expected to fall within an interval with the limits of $vv_{left}$ and $vv_{middle}$. That is why $vv_{right}$ will be replaced by $vv_{middle}$ and $vv_{middle}$ will be replaced by $vv_{toLeft}$ for the next iteration.

In case $pd_{toRight}$ is smaller than $pd_{middle}$, the minimum of the graph is expected to fall within an interval with the limits of $vv_{middle}$ and $vv_{right}$. That is why $vv_{left}$ will be replaced by $vv_{middle}$ and $vv_{middle}$ will be replaced by $vv_{toRight}$ for the next iteration.

Otherwise, the minimum of the graph is expected to fall within the limits $vv_{toLeft}$ and $vv_{toRight}$ and the search interval is simply narrowed by replacing $vv_{left}$ by $vv_{toLeft}$ and $vv_{right}$ by $vv_{toRight}$. This is the case in the example shown in FIG. 7d.

Figure 7E:
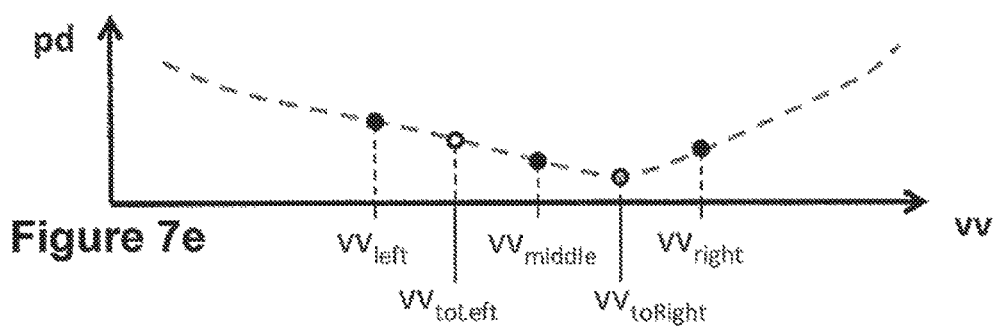
Figure 7F:
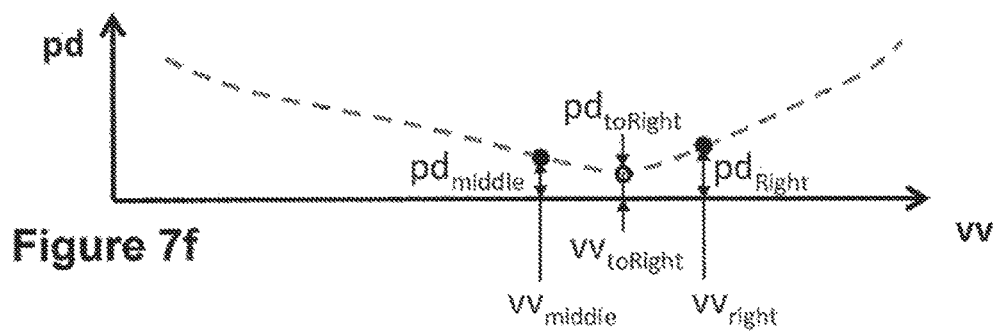

FIG. 7e shows the values $vv_{toLeft}$ and $vv_{toRight}$ in the next iteration. In this iteration, the smallest minimum possible distance occurs for $vv_{toRight}$, such that the range of values for vv in the next iteration as shown in FIG. 7f is limited by $vv_{middle}$ and $vv_{right}$ of the iteration of FIG. 7e.

Figure 7G:
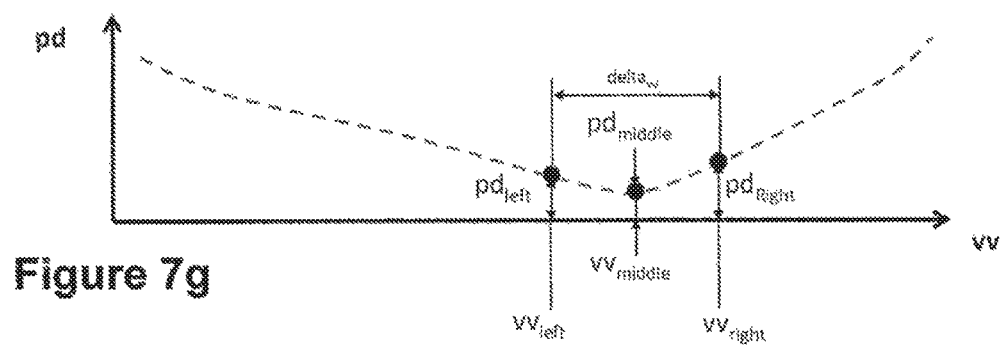

After some iterations, the distance between $vv_{left}$ and $vv_{right}$ will fall below a given threshold $delta_{vv}$ as shown in FIG. 7g and the search can be stopped. The value for $vv_{opt}$ will then lie somewhere between $vv_{left}$ and $vv_{right}$ and be known with a precision of $+/-0.5$ $delta_{vv}$. The value for $pd_{opt}$ will be close to $pd_{middle}$.

It shall be noted that if a plurality of sets of given parameters is provided, these sets of given parameters do not necessarily have to cover a four-dimensional parameter space, but can also represent a particular motion, such as the bending of a knee. In this case, the resulting set of contact positions represents this motion like it would be performed by the actual joint.

The present invention is not limited to a knee joint formed by a femur and a tibia as used in the foregoing description. On the contrary, the invention can be applied to any suitable joint.

A sequence of contact positions can for example be visualized by displaying a corresponding sequence of the 3D models assuming the contact positions on the display device 10.

It is claimed:

1. A computer implemented method for determining a contact position of a joint, which has six degrees of freedom, and which connects two bones and supports a range of relative movement between the two bones, comprising:
   acquiring a 3D model of each bone of the two bones;
   defining six parameters corresponding to the six degrees of freedom of the joint;
   acquiring four of the six parameters as fixed parameters;
   selecting initial values for the two remaining parameters of the six parameters, wherein the selecting of the initial values for the two remaining parameters is such that the 3D models of each bone are not in contact with each other;
   determining updated values of the two remaining parameters by varying the two remaining parameters of the six parameters from the selected initial values until achieving a relative position between the 3D models of each bone such that they are in contact with each other; and
   determining the contact position of the joint based on the four fixed parameters and the updated values of the two remaining parameters.

2. The method according to claim 1, wherein the two remaining parameters comprise a translational parameter and a rotational parameter.

3. The method according to claim 2, wherein an axis of rotation of the rotational parameter is perpendicular to a direction of the translational parameter.

4. The method according to claim 2, wherein the 3D models of each bone are considered as being in contact with each other when the rotational parameter and the translational parameter are selected such that a minimum possible distance between the 3D models of each bone in a direction of the translational parameter is minimized.

5. The method according to claim 4, further comprising calculating the rotational parameter for which the minimum possible distance is minimized by:
   (a) defining a range of values for the rotational parameter;
   (b) calculating a first value lying in the middle of the range of values;
   (c) calculating a second value lying in the middle between the lower boundary of the range of values and the first value;
   (d) calculating a third value lying in the middle between the upper boundary of the range of values and the first value;
   (e) determining a first minimum possible distance for the first value of the rotational parameter, a second minimum possible distance for the second value of the rotational parameter and a third minimum possible distance for the third value of the rotational parameter;
   (f) repeating steps (b) to (e) for a predetermined number of iterations with a new range of values, the new range of values having half the width of the current range of values and being centered about the one of the first, second or third values which results in the smallest of the first, second and third minimum possible distances; and
   (g) selecting the one of the first, second or third values which results in the smallest of the first, second and third minimum possible distance for the rotational parameter.

6. The method according to claim 2, wherein:
   the 3D models of each bone are moved towards each other along a direction of the translational parameter until there is a first contact point between surfaces of the two 3D models;
   the movement is continued until there is a second contact point between the surfaces of the 3D models; and
   the rotational parameter is then calculated such that the two 3D models of the two bones are in contact at two contact points.

7. The method according to claim 6, wherein:
   the rotational parameter is changed such that a difference of distances by which the first contact point and the second contact point are moved in the direction of the translational parameter by changing the rotational parameter equals the distance by which the 3D models are moved towards each other in the direction of the translational parameter between reaching the first contact point and the second contact point, and
   the translational parameter is amended such that the movement of the second contact point in the direction of the translational parameter, caused by the rotation about the rotational parameter, is compensated.

8. The method according to claim 6, wherein the varying the two remaining parameters of the six parameters is repeated in a further iteration, with the value of the rotation parameter determined in the preceding iteration being selected as the initial value of the rotational parameter in the further iteration.

9. The method according to claim 1, wherein when the 3D models of each bone touch over an area and not at a single contact point, the center of this area is chosen as a contact point.

10. The method of claim 1, further comprising defining a plurality of parameter sets for the four fixed parameters, and determining a contact position for each of the parameter sets.

11. The method according to claim 10, further comprising varying each fixed parameter in the parameter sets in steps within a given range.

12. The method according to claim 1, further comprising using collision detection techniques to determine whether there is a contact between the surfaces of the 3D models of each bone.

13. A non-transitory computer readable storage medium comprising a computer program which, when running on a computer or when loaded onto a computer, causes the computer to perform a method for determining a contact position of a joint, which has six degrees of freedom, and which connects two bones and supports a range of relative movement between the two bones, the method comprising:
   acquiring a 3D model of each bone of the two bones;
   defining six parameters corresponding to the six degrees of freedom;
   acquiring four of the six parameters as fixed parameters;
   selecting initial values for the two remaining parameters such that the 3D models of each of the two bones are not in contact with each other;

wherein the two remaining parameters comprise a translational parameter and a rotational parameter;

determining updated values of the two remaining parameters by varying the two remaining parameters from the selected initial values until achieving a relative position between the 3D models of the two bones such that they are in contact with each other;

determining the contact position of the joint based on the four fixed parameters and the updated values of the two remaining parameters;

wherein determining the contact position of the joint between the two bones includes moving the two bones towards each other along a direction of the translational parameter until there is a first contact point between surfaces of the two bones;

continuing the movement until there is a second contact point between the surfaces of the two bones; and calculating the rotational parameter such that the two 3D models of the two bones are in contact at two contact points.

14. A computer comprising the non-transitory computer readable storage medium according to claim 13.

15. A method for determining a contact position of a knee joint, which has six degrees of freedom, and which connects a first bone of an associated patient with a second bone of the associated patient and which supports a range of relative movement between the first and second bones, the first bone being a femur and the second bone being the tibia, wherein the six parameters define one or more of a translational shift between the first and second bones and a rotational shift between the first and second bones, the method comprising:

acquiring a 3D model of each of the first and second bones;

defining six parameters corresponding to the six degrees of freedom;

acquiring n of the six parameters as n fixed parameters;

the acquiring the n parameters includes acquiring one or more of the parameters defining the translational shift between the first and second bones, and acquiring one or more of the parameters defining the rotational shift between the first and second bones;

selecting initial values for the 6-n remaining parameters of the six parameters where n is an integer in the range of 2-5 such that the 3d models of each of the two bones are not in contact with each other;

determining updated values of the 6-n remaining parameters by varying the 6-n remaining parameters of the six parameters from the selected initial values until achieving a virtual relative position between the 3D models of each bone such that they are in contact with each other; and determining the contact position of the joint based on the n fixed parameters and the updated values of the 6-n remaining parameters.

16. The method according to claim 15, wherein: the acquiring the one or more of the parameters defining the translational shift between the first and second bones comprises one or more of:

acquiring a parameter defining a translational shift in a proximodistal (pd) direction between the first and second bones;

acquiring a parameter defining a translational shift in a anterioposterior (ap) direction between the first and second bones; and/or acquiring a parameter defining a translational shift in a mediolateral (ml) direction between the first and second bones; and the acquiring the one or more of the parameters defining the rotational shift between the first and second bones comprises one or more of:

acquiring a parameter defining a rotational shift in a flexion/extension (fe) angle between the first and second bones;

acquiring a parameter defining a rotational shift in an internal/external (ie) angle between the first and second bones; and/or acquiring a parameter defining a rotational shift in a *varus*/valgus (vv) angle between the first and second bones.

17. The method according to claim 16, wherein: the acquiring the n parameters as the n fixed parameters comprises:

acquiring the parameter defining the translational shift in the anterioposterior (ap) direction between the first and second bones;

acquiring the parameter defining the translational shift in the mediolateral (ml) direction between the first and second bones;

acquiring the parameter defining the rotational shift in the flexion/extension (fe) angle between the first and second bones; and acquiring the parameter defining the rotational shift in the internal/external (ie) angle between the first and second bones; and the varying the 6-n remaining parameters comprises varying the parameter defining the translational shift in the proximodistal (pd) direction between the first and second bones and varying the parameter defining the rotational shift in the varus/valgus (vv) angle between the first and second bones until achieving the relative position between the 3D models of each bone such that they are in contact with each other.

* * * * *